United States Patent
McDonald et al.

(10) Patent No.: US 8,406,896 B2
(45) Date of Patent: Mar. 26, 2013

(54) MULTI-ELEMENT CONTACT ASSEMBLIES FOR ELECTRICAL STIMULATION SYSTEMS AND SYSTEMS AND METHODS OF MAKING AND USING

(75) Inventors: Matthew Lee McDonald, Glendale, CA (US); John Michael Barker, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 248 days.

(21) Appl. No.: 12/494,077

(22) Filed: Jun. 29, 2009

(65) Prior Publication Data
US 2010/0331934 A1  Dec. 30, 2010

(51) Int. Cl.
*A61N 1/05* (2006.01)
(52) U.S. Cl. ........ 607/116; 607/117; 607/119; 600/372; 600/373; 600/377
(58) Field of Classification Search ............ 607/46, 607/116, 117, 119, 122; 600/372, 373, 374, 600/377, 378
See application file for complete search history.

(56) References Cited

U.S. PATENT DOCUMENTS

| 4,488,561 A | | 12/1984 | Doring | |
|---|---|---|---|---|
| 4,630,611 A | | 12/1986 | King | |
| 4,835,853 A | * | 6/1989 | Hirschberg | 29/854 |
| 4,938,822 A | * | 7/1990 | Peers-Trevarton | 156/144 |
| 5,007,436 A | | 4/1991 | Smits | |
| 5,115,818 A | | 5/1992 | Holleman et al. | |
| 5,251,643 A | * | 10/1993 | Osypka | 607/122 |
| 5,330,522 A | * | 7/1994 | Kreyenhagen | 607/122 |
| 5,342,414 A | | 8/1994 | Mehra | |
| 5,374,285 A | * | 12/1994 | Vaiani et al. | 607/117 |

(Continued)

FOREIGN PATENT DOCUMENTS

| EP | 0057877 A1 | 8/1982 |
|---|---|---|
| EP | 0426089 A2 | 5/1991 |

(Continued)

OTHER PUBLICATIONS

International Search Report and Written Opinion for International Patent Application No. PCT/US2010/039544, mailed on Aug. 31, 2010.

(Continued)

*Primary Examiner* — Carl H Layno
*Assistant Examiner* — Eugene Wu
(74) *Attorney, Agent, or Firm* — Frommer Lawrence & Haug LLP; Patrick R. Turner

(57) ABSTRACT

An implantable lead includes a lead body having a plurality of electrodes disposed on a distal end of the lead body, a plurality of terminals disposed on a proximal end of the lead body, and a plurality of conductors disposed along the lead body such that each conductor electrically couples at least one of the electrodes to at least one of the terminals. At least one of the electrodes or terminals includes a multi-element contact assembly. The multi-element contact assembly includes at least one conductive inner element and at least one conductive outer element disposed over the inner element. At least one of the plurality of conductors is electrically coupled to one of the multi-element contact assemblies such that the conductor is positioned against the at least one inner element. The at least one outer element includes a region that is in contact with the at least one inner element.

21 Claims, 9 Drawing Sheets

U.S. PATENT DOCUMENTS

| | | | |
|---|---|---|---|
| 5,458,629 A | 10/1995 | Baudino et al. | |
| 5,514,172 A | 5/1996 | Mueller | |
| 5,516,396 A * | 5/1996 | Maurer et al. | 607/138 |
| 5,534,022 A | 7/1996 | Hoffmann et al. | |
| 5,545,201 A | 8/1996 | Helland et al. | |
| 5,580,699 A | 12/1996 | Layman et al. | |
| 5,713,945 A | 2/1998 | Fischer et al. | |
| 5,755,762 A | 5/1998 | Bush | |
| 5,782,892 A | 7/1998 | Castle et al. | |
| 5,869,804 A | 2/1999 | Mueller et al. | |
| 5,871,530 A | 2/1999 | Williams et al. | |
| 5,902,329 A | 5/1999 | Hoffmann et al. | |
| 5,919,222 A | 7/1999 | Hjelle et al. | |
| 5,954,759 A | 9/1999 | Swoyer et al. | |
| 5,991,650 A | 11/1999 | Swanson et al. | |
| 6,016,436 A | 1/2000 | Bischoff et al. | |
| 6,021,354 A | 2/2000 | Warman et al. | |
| 6,032,061 A * | 2/2000 | Koblish | 600/372 |
| 6,038,463 A | 3/2000 | Laske et al. | |
| 6,144,870 A * | 11/2000 | Griffin, III | 600/374 |
| 6,181,969 B1 | 1/2001 | Gord | |
| 6,181,971 B1 * | 1/2001 | Doan | 607/116 |
| 6,183,305 B1 | 2/2001 | Doan et al. | |
| 6,185,463 B1 | 2/2001 | Baudino | |
| 6,192,280 B1 | 2/2001 | Sommer et al. | |
| 6,210,339 B1 | 4/2001 | Kiepen et al. | |
| 6,216,045 B1 | 4/2001 | Black et al. | |
| 6,289,250 B1 | 9/2001 | Tsuboi et al. | |
| 6,289,251 B1 | 9/2001 | Huepenbecker et al. | |
| 6,295,475 B1 | 9/2001 | Morgan | |
| 6,366,820 B1 * | 4/2002 | Doan et al. | 607/122 |
| 6,370,434 B1 | 4/2002 | Zhang et al. | |
| 6,440,488 B2 | 8/2002 | Griffin, III et al. | |
| 6,505,401 B1 | 1/2003 | Doan | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,658,289 B2 | 12/2003 | Helland | |
| 6,741,892 B1 | 5/2004 | Meadows et al. | |
| 6,757,970 B1 | 7/2004 | Kuzma et al. | |
| 6,882,887 B1 | 4/2005 | Shelchuk et al. | |
| 6,952,616 B2 | 10/2005 | Wessman et al. | |
| 6,968,237 B2 | 11/2005 | Doan et al. | |
| 6,978,185 B2 | 12/2005 | Osypka | |
| 6,990,378 B1 | 1/2006 | Algee | |
| 6,999,821 B2 | 2/2006 | Jenney et al. | |
| 7,031,774 B1 | 4/2006 | Doan et al. | |
| 7,039,470 B1 | 5/2006 | Wessman | |
| 7,047,081 B2 | 5/2006 | Kuzma | |
| 7,047,627 B2 | 5/2006 | Black et al. | |
| 7,072,719 B2 | 7/2006 | Vinup et al. | |
| 7,130,700 B2 * | 10/2006 | Gardeski et al. | 607/122 |
| 7,184,838 B2 | 2/2007 | Cross, Jr. | |
| 7,184,840 B2 | 2/2007 | Stolz et al. | |
| 7,231,259 B2 | 6/2007 | Jenney et al. | |
| 7,239,922 B1 * | 7/2007 | Boogaard et al. | 607/116 |
| 7,244,150 B1 | 7/2007 | Brase et al. | |
| 7,286,882 B2 | 10/2007 | Cole | |
| 7,319,904 B2 | 1/2008 | Cross, Jr. et al. | |
| 7,330,764 B2 | 2/2008 | Swoyer et al. | |
| 7,389,149 B2 | 6/2008 | Rossing et al. | |
| 7,421,295 B2 | 9/2008 | Osypka | |
| 7,467,017 B2 | 12/2008 | Osypka | |
| 7,546,165 B2 | 6/2009 | Zarembo et al. | |
| 7,957,818 B2 * | 6/2011 | Swoyer | 607/116 |
| 2002/0138123 A1 | 9/2002 | Casas-Bejar et al. | |
| 2003/0083697 A1 | 5/2003 | Baudino et al. | |
| 2003/0088301 A1 | 5/2003 | King | |
| 2003/0114905 A1 | 6/2003 | Kuzma | |
| 2003/0199956 A1 | 10/2003 | Struble et al. | |
| 2004/0059392 A1 | 3/2004 | Parramon et al. | |
| 2004/0106964 A1 | 6/2004 | Fischer et al. | |
| 2004/0127968 A1 * | 7/2004 | Kuzma et al. | 607/137 |
| 2004/0243205 A1 | 12/2004 | Keravel et al. | |
| 2005/0004639 A1 | 1/2005 | Erickson | |
| 2005/0027338 A1 | 2/2005 | Hill | |
| 2005/0113899 A1 | 5/2005 | Cross | |
| 2005/0131507 A1 | 6/2005 | Sundberg | |
| 2005/0165465 A1 | 7/2005 | Pianca et al. | |
| 2006/0095107 A1 | 5/2006 | Osypka | |
| 2006/0122681 A1 | 6/2006 | Kroll et al. | |
| 2006/0224224 A1 | 10/2006 | Muhlenberg et al. | |
| 2007/0038279 A1 | 2/2007 | Fifer et al. | |
| 2007/0142890 A1 | 6/2007 | Zarembo et al. | |
| 2007/0150007 A1 | 6/2007 | Anderson et al. | |
| 2007/0150036 A1 | 6/2007 | Anderson | |
| 2007/0161294 A1 | 7/2007 | Brase et al. | |
| 2007/0168007 A1 * | 7/2007 | Kuzma et al. | 607/116 |
| 2007/0219595 A1 | 9/2007 | He | |
| 2007/0239243 A1 | 10/2007 | Moffitt et al. | |
| 2007/0299490 A1 | 12/2007 | Yang et al. | |
| 2008/0071320 A1 | 3/2008 | Brase | |
| 2008/0132982 A1 | 6/2008 | Gerber | |
| 2008/0147155 A1 | 6/2008 | Swoyer et al. | |
| 2008/0243218 A1 | 10/2008 | Bottomley et al. | |
| 2008/0262582 A1 | 10/2008 | Alexander et al. | |
| 2008/0262585 A1 | 10/2008 | Alexander et al. | |
| 2008/0269856 A1 | 10/2008 | Cross et al. | |
| 2008/0269857 A1 | 10/2008 | Cross et al. | |
| 2008/0269858 A1 | 10/2008 | Cross et al. | |
| 2009/0054936 A1 | 2/2009 | Eggen et al. | |
| 2009/0054960 A1 | 2/2009 | Stolen et al. | |
| 2009/0088811 A1 | 4/2009 | Wulfman | |
| 2009/0187221 A1 | 7/2009 | DiGiore et al. | |
| 2009/0222073 A1 | 9/2009 | Flowers et al. | |
| 2009/0222074 A1 | 9/2009 | Zarembo et al. | |

FOREIGN PATENT DOCUMENTS

| | | |
|---|---|---|
| EP | 1017445 A1 | 7/2000 |
| WO | WO-9911319 A1 | 3/1999 |
| WO | WO-2007127997 A2 | 11/2007 |
| WO | WO-2007127998 A2 | 11/2007 |
| WO | WO-2007133930 A2 | 11/2007 |

OTHER PUBLICATIONS

U.S. Appl. No. 11/238,240, filed Sep. 29, 2005.

* cited by examiner

MULTI-ELEMENT CONTACT ASSEMBLIES FOR ELECTRICAL STIMULATION SYSTEMS AND SYSTEMS AND METHODS OF MAKING AND USING

FIELD

The present invention is directed to the area of implantable electrical stimulation systems and methods of making and using the systems. The present invention is also directed to implantable electrical stimulation leads (and lead extensions) having multi-element contact assemblies, as well as methods of making and using the leads (and lead extensions), multi-element contact assemblies, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Conventional implanted electrical stimulation systems are often incompatible with magnetic resonance imaging ("MRI") due to the large radio frequency ("RF") pulses used during MRI. The RF pulses can generate transient signals in the conductors and electrodes of an implanted lead. These signals can have deleterious effects including, for example, unwanted heating of the tissue causing tissue damage, induced currents in the lead, or premature failure of electronic components.

BRIEF SUMMARY

In one embodiments, an implantable lead includes a lead body having a distal end, a proximal end, and a longitudinal length. A plurality of electrodes are disposed on the distal end of the lead body. A plurality of terminals are disposed on the proximal end of the lead body. A plurality of conductors are disposed in the lead body such that each conductor electrically couples at least one of the electrodes to at least one of the terminals. At least one of the electrodes or at least one of the terminals includes a multi-element contact assembly. The multi-element contact assembly includes at least one conductive inner element and at least one conductive outer element disposed over the inner element. At least one of the plurality of conductors is electrically coupled to one of the multi-element contact assemblies such that the conductor is positioned against the at least one inner element. The at least one outer element includes a region that is in contact with the at least one inner element.

In another embodiment, a method for forming an implantable lead includes disposing a plurality of elongated conductors in a lead body of the lead such that ends of the conductors extend from ends of the lead body. A multi-element contact assembly is disposed at one of the ends of the lead body. The multi-element contact assembly includes an inner element and an outer element disposed over the inner element. An end of one of the plurality of conductors is disposed into the multi-element contact assembly such that the conductor is positioned against the at least one inner element. A region of the at least one outer element is contacted with the at least one inner element.

In yet another embodiment, a method for forming an implantable lead includes disposing a plurality of elongated conductors in a lead body of the lead such that ends of the conductors extend from ends of the lead body. Each of the ends of the conductors extending from one end of the lead body are physically attached to one of a different one of a plurality of inner elements. A different one of a plurality of outer elements are disposed individually over each of the inner elements to form a plurality of multi-element contact assemblies. Each of the multi-element contact assemblies includes a one of the outer elements disposed around a one of the inner elements. Each of the inner elements of the multi-element contact assemblies are contacted to the corresponding outer elements.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads (and lead extensions) having multi-element contact assemblies, as well as methods of making and using the leads (and lead extensions), multi-element contact assemblies, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; and U.S. patent application Ser. Nos. 10/353,101, 10/503,281, 11/238,240; 11/319,291; 11/327,880; 11/375,638; 11/393,991; and 11/396,309, all of which are incorporated by reference.

Figure 1:
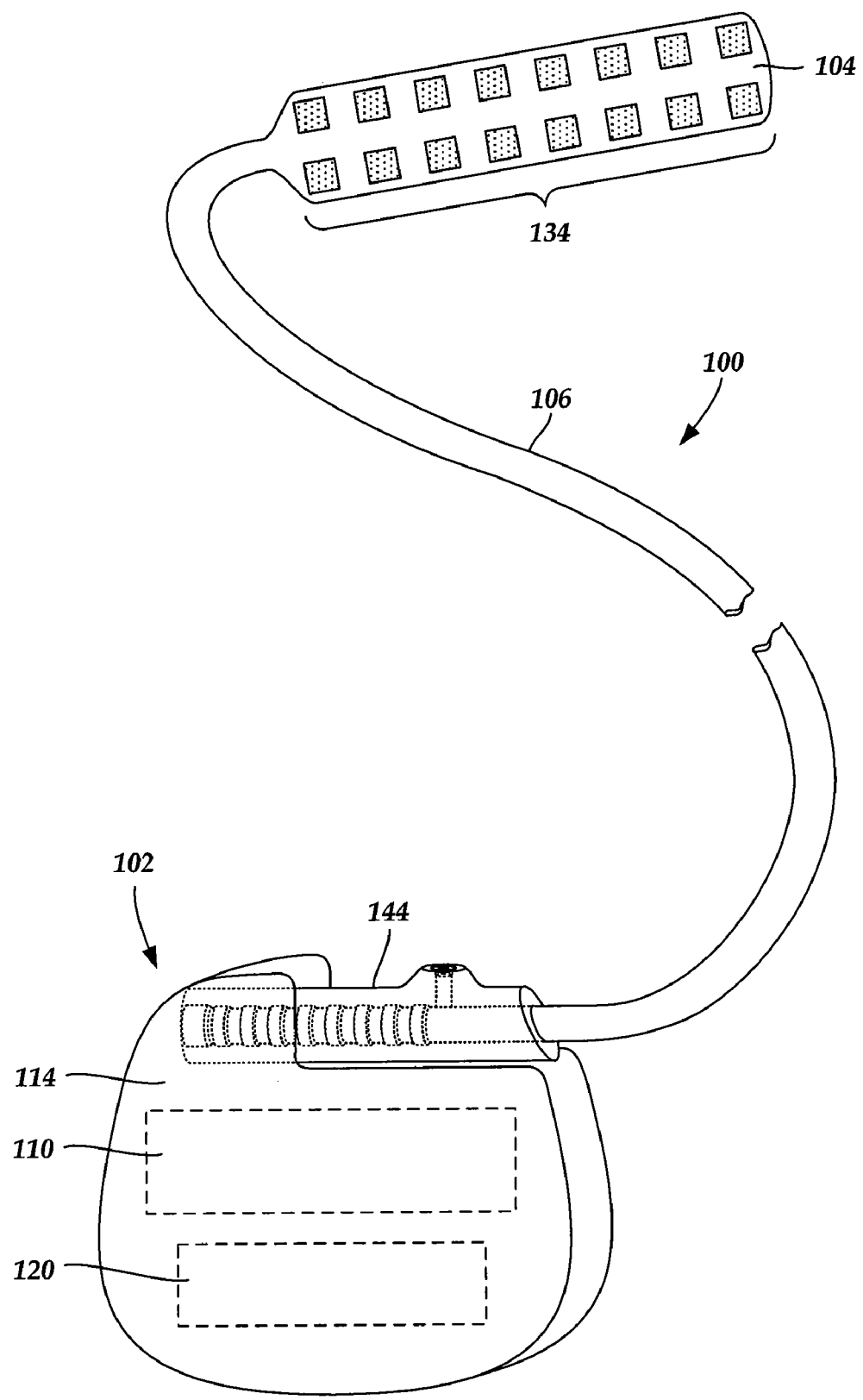
FIG. 1 is a schematic view of one embodiment of an electrical stimulation system, according to the invention.
Figure 2:
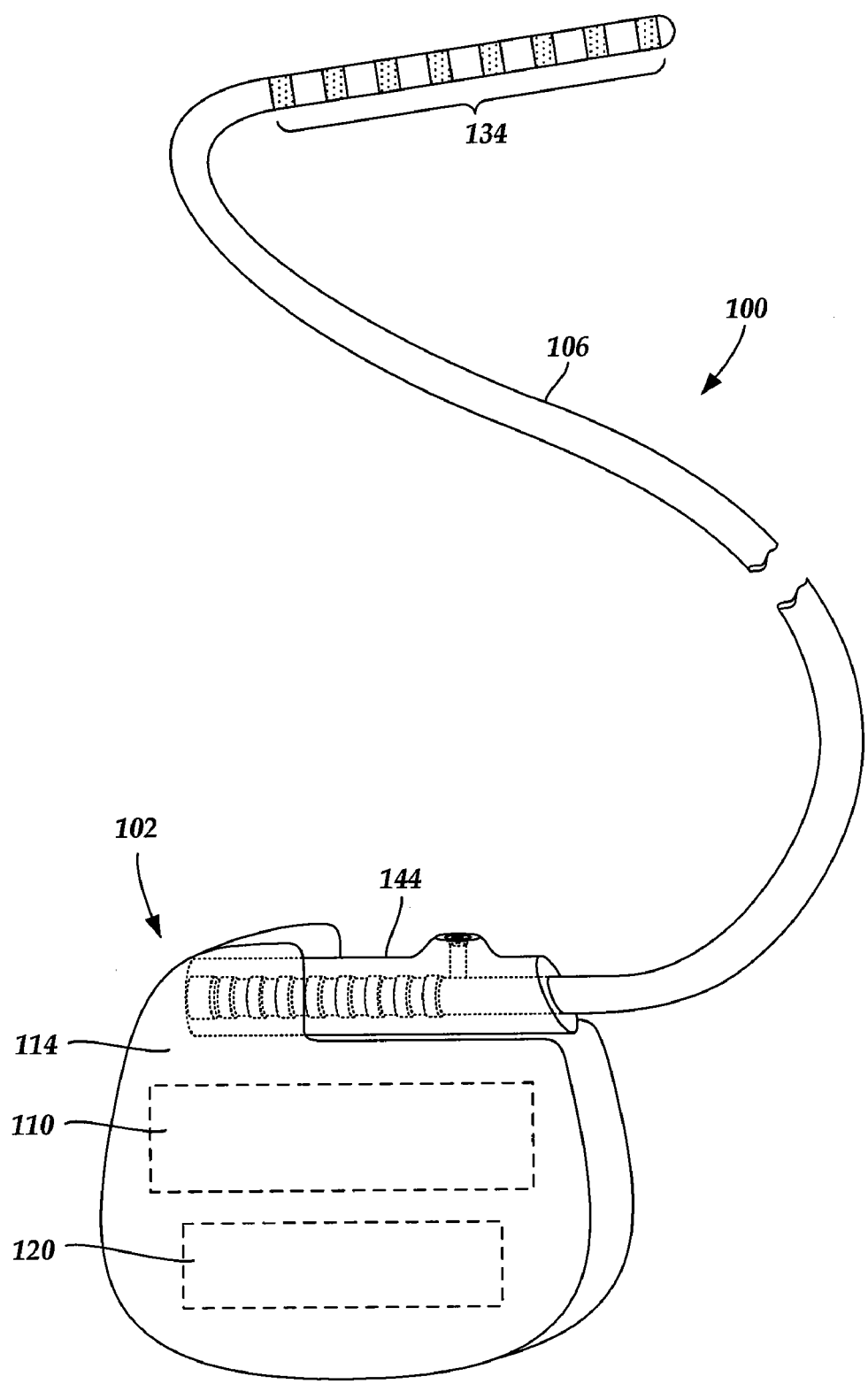
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and at least one lead body 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. The control module 102 typically includes a connector 144 (FIGS. 2 and 3A, see also 322 and 350 of FIG. 3B) into which the proximal end of the one or more lead bodies 106 can be plugged to make an electrical connection via conductive contacts on the control module 102 and terminals (e.g., 310 in FIG. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 312 (see FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, polyetheretherketone ("PEEK"), epoxy, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A and 336 of FIG. 3B) are typically disposed at the proximal end of the one or more lead bodies 106 for connection to corresponding conductive contacts (e.g., 314 in FIG. 3A and 340 of FIG. 3B) in connectors (e.g., 144 in FIGS. 1-3A and 322 and 350 of FIG. 3B) disposed on, for example, the control module 102 (or to other devices, such as conductive contacts on a lead extension, an operating room cable, or an adaptor). Conductive wires ("conductors") (not shown) extend from the terminals (e.g., 310 in FIG. 3A and 336 of FIG. 3B) to the electrodes 134. Typically, one or more electrodes 134 are electrically coupled to a terminal (e.g., 310 in FIG. 3A and 336 of FIG. 3B). In some embodiments, each terminal (e.g., 310 in FIG. 3A and 336 of FIG. 3B) is only connected to one electrode 134. The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 3A:
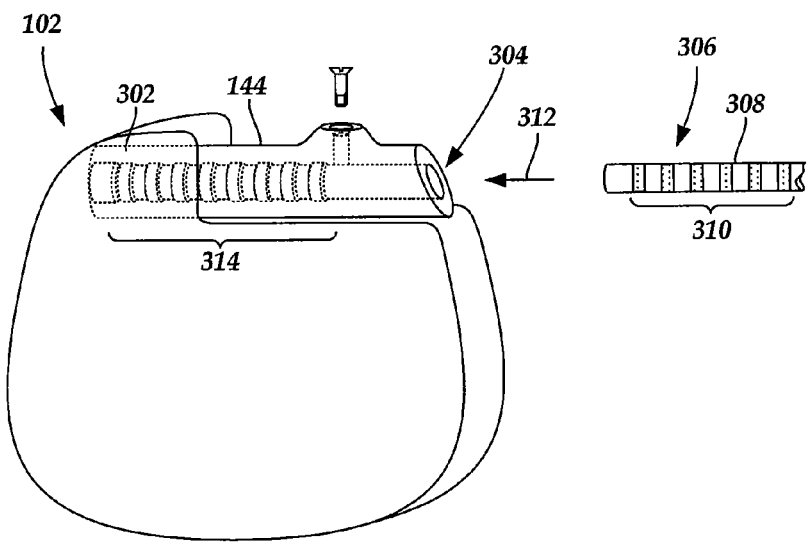
FIG. 3A is a schematic view of one embodiment of a proximal portion of a lead and a control module of an electrical stimulation system, according to the invention.

In at least some embodiments, leads are coupled to connectors disposed on control modules. In FIG. 3A, a lead 308 is shown configured and arranged for insertion to the control module 102. The connector 144 includes a connector housing 302. The connector housing 302 defines at least one port 304 into which a proximal end 306 of a lead 308 with terminals 310 can be inserted, as shown by directional arrow 312. The connector housing 302 also includes a plurality of conductive contacts 314 for each port 304. When the lead 308 is inserted into the port 304, the conductive contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat. No. 7,244,150 and U.S. patent application Ser. No. 11/532,844, which are incorporated by reference.

Figure 3B:
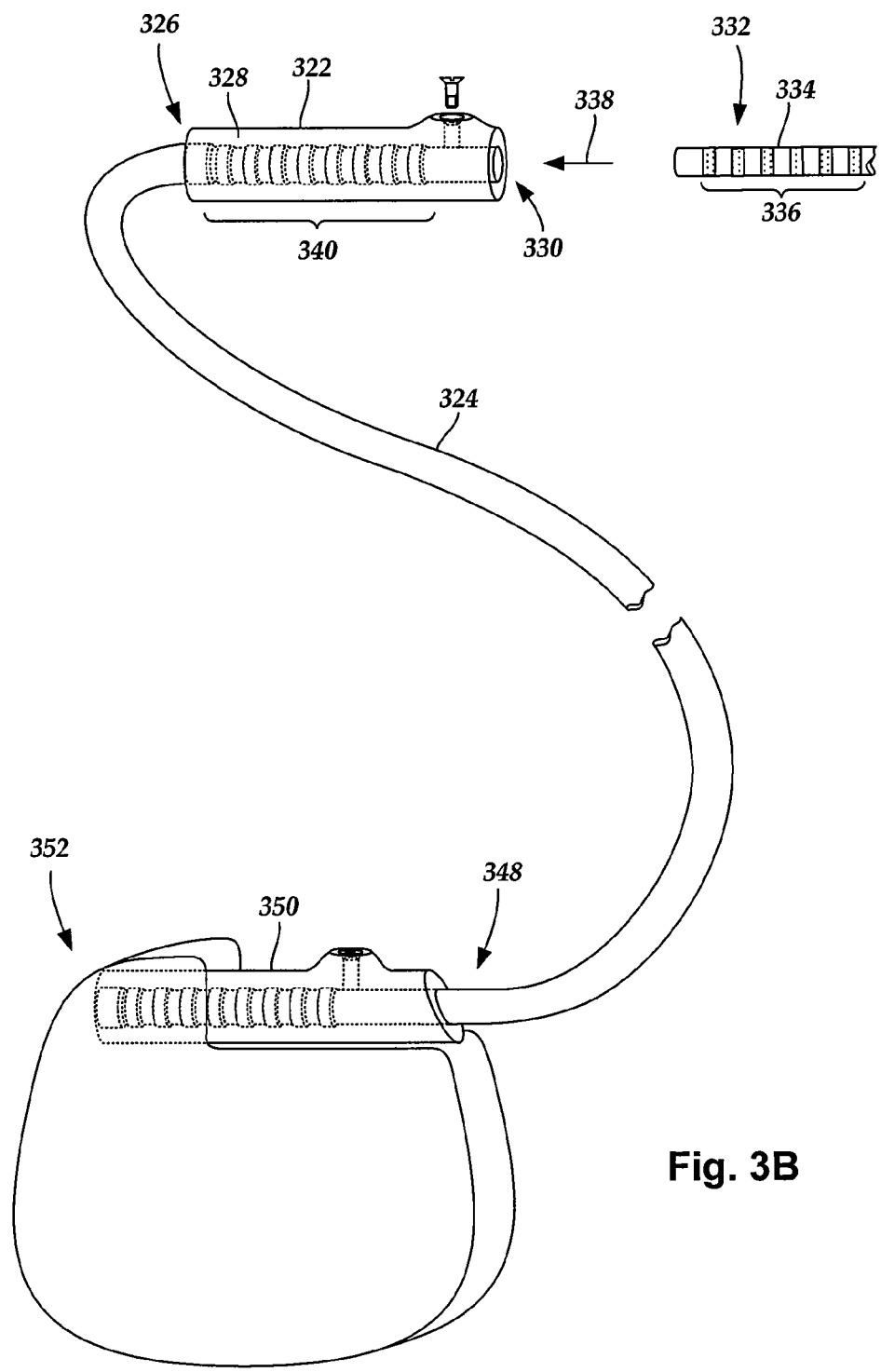
FIG. 3B is a schematic view of one embodiment of a proximal portion of a lead and a lead extension of an electrical stimulation system, according to the invention.

In FIG. 3B, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead 334 with terminals 336 can be inserted, as shown by directional arrow 338. The connector housing 328 also includes a plurality of conductive contacts 340. When the lead 334 is inserted into the port 330, the conductive contacts 340 disposed in the connector housing 328 can be aligned with the terminals 336 on the lead 334 to electrically couple the lead extension 324 to the electrodes (134 of FIG. 1) disposed at a distal end (not shown) of the lead 334.

In at least some embodiments, the proximal end of a lead extension is similarly configured and arranged as a proximal end of a lead. The lead extension 324 may include a plurality of conductive wires (not shown) that electrically couple the conductive contacts 340 to a proximal end 348 of the lead extension 324 that is opposite to the distal end 326. In at least some embodiments, the conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. As an example, in FIG. 3B the proximal end 348 of the lead extension 324 is inserted into a connector 350 disposed in a control module 352.

One or more of the conductors connecting at least one terminal to an electrode (or other conductive contact) can be arranged in a conductor path to eliminate or reduce the effect of RF irradiation, such as that generated during magnetic resonance imaging ("MRI"). The conductor path includes a plurality of units arranged in series. In some embodiments, the units are disposed along a single continuous conductor. In other embodiments, the units are separate conductive elements electrically coupled together.

Each unit includes at least three conductor segments that at least partially overlap one another to form a multi-coil region. First, each unit includes a first conductor segment that extends in a first direction along a longitudinal length of an elongated member (e.g., a lead or lead extension) from a beginning point to a first position. Second, each unit includes a second conductor segment that extends from the first position back towards (and possibly past) the beginning point to a second position. Third, each unit includes a third conductor segment that extends in the first direction from the second position to an endpoint. In at least some embodiments, the first position is between the second position and the endpoint. In at least some embodiments, the second position is between the beginning point and the first position. In at least some embodiments, the unit may include a single-coil region flanking at least one end of the multi-coil region.

The units may be electrically continuous such that the endpoint of a first unit is the beginning point of the next consecutive unit. At least one of the beginning points may be a terminal or an electrode (or other conductive contact). Likewise, at least one of the endpoints may be a terminal or an electrode (or other conductive contact). In preferred embodiments, the conductor segments are each coiled. In at least some embodiments, the conductor segments are coiled around a conductor placement sleeve. In at least some embodiments, the conductor placement sleeve defines a lumen that optionally is configured and arranged to receive a stiffening member (e.g., a stylet, or the like).

In at least some embodiments, at least one of the first, second, or third conductor segments is substantially straight. In at least some embodiments, the first and third conductor segments are substantially straight and the second conductor segment is coiled. In at least some other embodiments, all three conductor segments are substantially straight. It will be understood that the term "substantially straight conductor segment" means that the conductor segment is not coiled. A "substantially straight conductor segment" may be curved, particularly when the lead itself is curved (see, for example, FIG. 1).

In at least some embodiments, the conductor segments are all formed from the same length of conductive material (e.g., wire or the like). The conductors may have a single filament or be multi-filar. In preferred embodiments, the conductors are multi-filar. In at least some embodiments, two or more of the conductor segments can be individual pieces of conductive material that are electrically coupled (e.g., soldered or welded) together. In at least some embodiments, a layer of insulation ("conductor insulation") is disposed over each of the conductor segments.

In at least some embodiments, the length of conductor used in the second conductor segment is at least 1.5, 1.75, 1.9, 2, 2.1, 2.25, or 2.5 times the length of either the first conductor segment or the third conductor segment. It will be recognized, however, that this ratio of conductor-segment lengths may vary among embodiments, particularly if the thickness of the conductor or thickness of the layer of conductor insulation is different for the different segments.

Figure 4:
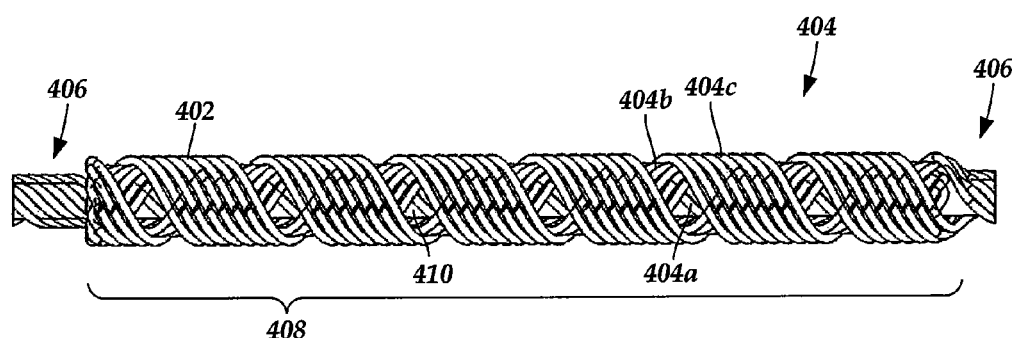
FIG. 4 is a schematic side view of one embodiment of portions of a plurality of conductors disposed along a conductor placement sleeve, the conductors configured into units, according to the invention.

FIG. 4 schematically illustrates one embodiment of a plurality of conductors 402. The conductors 402 are configured into a plurality of units, such as unit 404. Each unit includes a first conductor segment 404*a*, a second conductor segment 404*b*, and a third conductor segment 404*c*. In at least some embodiments, conductor insulation is disposed over the conductors 402 to electrically isolate each of the conductors 402 from one another.

Many different numbers of units may be disposed along longitudinal lengths of the conductors 402 including, for example, two, three, four, five, six, seven, eight, nine, ten, twelve, fifteen, twenty, twenty-five, thirty, forty, fifty, or more units. It will be understood that many other numbers of units may be employed as well. When a plurality of units are coupled together in series along a longitudinal length of one or more conductors, the plurality of units form a repeating series of single-coil regions, such as the single-coil regions 406, separated from one another by a multi-coil region, such as the multi-coil region 408.

In at least some embodiments, the conductors 402 are disposed along a conductor placement sleeve 410. The conductor placement sleeve 410 can be formed from any suitable biocompatible material including, for example, one or more polymers. In at least some embodiments, conductor insulation is disposed over the conductors 402 to encapsulate the conductors 402 and electrically isolate the conductors 402 from one another.

In at least some embodiments, one or more conductors having one or more units may be disposed in an elongated member (e.g., a lead or lead extension). In at least some embodiments, the ends of the conductors 402 can be coupled to terminals, electrodes, or conductive contacts. In preferred embodiments, each of the conductors in an elongated member are configured into units. In at least some embodiments, only a subset of the conductors disposed in an elongated member include one or more units, the remaining conductors having a different arrangement (for example, a single conductor segment between the terminal(s) and electrode(s)/conductive contact(s)).

Figure 5:
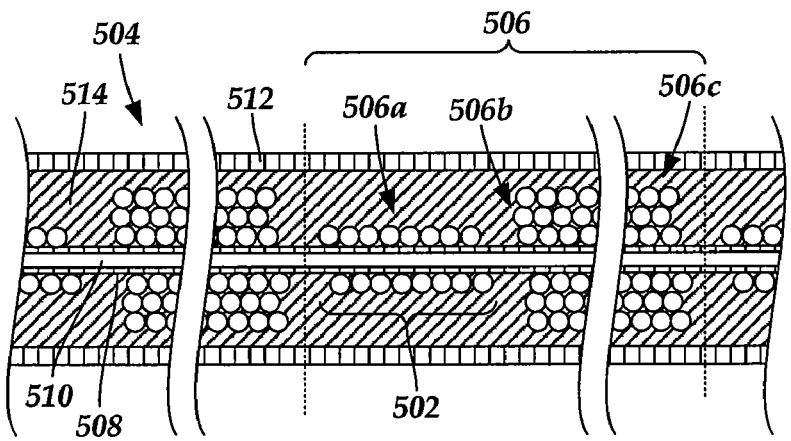
FIG. 5 is a schematic longitudinal cross-sectional view of one embodiment of portions of a plurality of conductors disposed in an elongated member, according to the invention.

Conductors, such as the conductors 402, may be disposed in a lumen of an elongated member (e.g., a lead, lead extension, or the like). FIG. 5 is a schematic longitudinal cross-sectional view of one embodiment of portions of a plurality of conductors 502 disposed in an elongated member 504. The illustrated portions of the conductors 502 includes unit 506, shown between two vertical dotted lines. Unit 506 includes a first conductor segment 506a, a second conductor segment 506b, and a third conductor segment 506c. In at least some embodiments, the conductors 502 are disposed over a conductor placement sleeve 508. In at least some embodiments, the conductor placement sleeve 508 defines a lumen 510. The elongated member 504 includes a body 512 and a lumen 514 into which the conductors 502 are disposed.

Figure 6A:
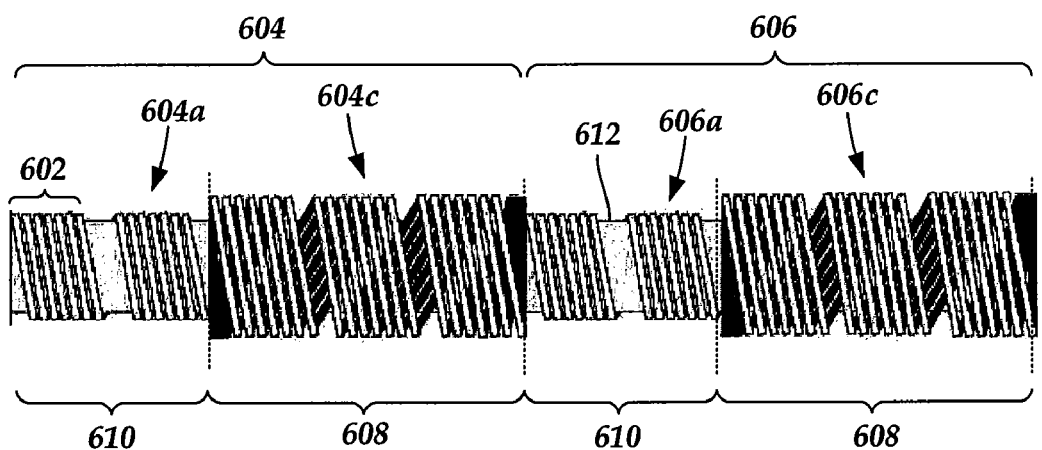
FIG. 6A is a schematic side view of one embodiment of a plurality of portions of conductors formed into two units that include alternating single-coil regions and multi-coil regions, according to the invention.

FIG. 6A schematically illustrates a side view of one embodiment of a plurality of conductors 602 each including units 604 and 606. In FIG. 6A, the first, second, and third conductor segments 604a, 604b (not shown in FIG. 6A), and 604c, respectively, of the unit 604, and the first, second, and third conductor segments 606a, 606b (not shown in FIG. 6A), and 606c, respectively, of the unit 606, are each coiled. The conductors 602 are arranged such that the conductors include multi-coil regions 608 and single-coil regions 610. In at least some embodiments, the conductors 602 may be coiled around one or more objects, such as a conductor placement sleeve 612.

Figure 6B:
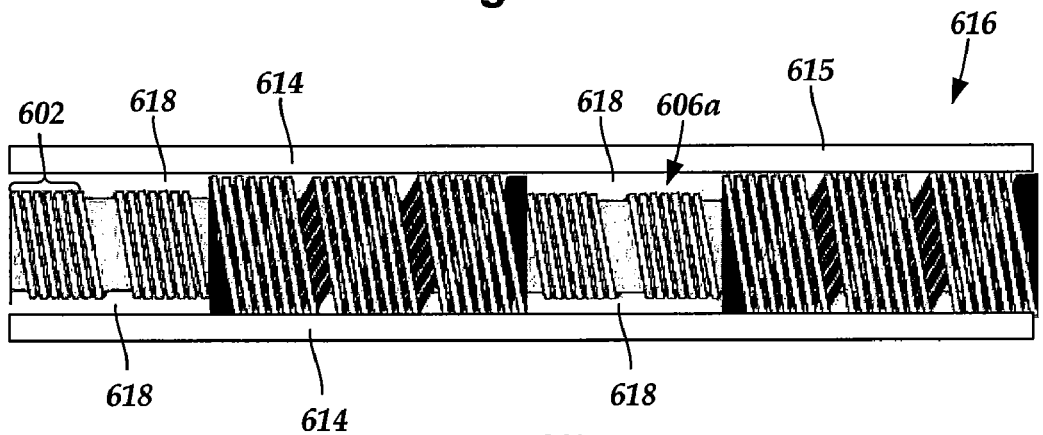
FIG. 6B is a schematic longitudinal cross-sectional view of one embodiment of the portions of conductors of FIG. 6A, according to the invention.

FIG. 6B is a schematic longitudinal cross-sectional view of the plurality of conductors 602 disposed in an outer layer 614 of a body 615 of a lead 616. When the outer layer 614 of the body 615 is isodiametric along the longitudinal length of the lead 616, open spaces 618 may form between the single-coil regions, such as single-coil region 606a, and the outer layer 614.

Typically, one or more contacts (e.g., terminals, electrodes, connective contacts, or the like) are disposed at opposing ends of an elongated member (e.g., a lead, a lead extension, or the like). The contacts disposed on opposite ends of the elongated member are electrically coupled together by elongated conductors extending along a longitudinal length of the elongated member. For example, terminals disposed on a proximal end of the conductor may be coupled, via conductors, to electrodes (or connective contacts) disposed on a distal end of the elongated member. During formation of the elongated member, the conductors may be disposed along a body of the elongated member in any number of different arrangements including, for example, configured into one or more units (as described above with reference to FIGS. 4-6B), wrapped around a sleeve or mandrel, extending substantially straight, disposed in one or more conductor-carrying elements, or the like).

It is desirable that the connections between the conductors and the contacts be strong enough to maintain a viable electrical connection during implantation and throughout the operational life of the electrical stimulation system within a patient. A loss of electrical connection between a conductor and a contact may result in a loss of therapeutic stimulation and may even necessitate an undesired explantation of the electrical stimulation system from the patient.

The connection between the conductor and the contact is sometimes made by a heat-related method of coupling (e.g., laser welding, resistance welding, brazing, soldering, or the like). A heat-related method of coupling alone, however, may not provide sufficient strength to maintain an electrical connection between the conductor and the contact throughout the operational life of the electrical stimulation system.

In some cases the conductor may also be mechanically clamped to the contact. Heat produced by the heat-related method of coupling, however, typically anneals the contact in a region of the contact in immediate proximity to the site of the heat-related coupling. The annealing may reduce the tensile strength of the conductor. One known attempt to separate the mechanical clamping from the heat-related coupling involved crimping sleeves to the ends of conductors, and then coupling the sleeves to the contacts. Unfortunately, manufacturing and handling sleeves that are small enough for clamping to the ends of conductors is tedious and complex.

In at least some embodiments, multi-element contact assemblies ("contact assemblies") are employed to electrically couple with contacts. The contact assemblies include a rigid (or semi-rigid), cylindrically-shaped outer element and a rigid (or semi-rigid) inner element that is disposed in the outer element. In at least some embodiments, the inner element is disposed concentrically in the outer element.

The contacts electrically couple to the contact assemblies by positioning the conductors against the inner elements and contacting the outer elements and the inner elements. In at least some embodiments, the outer elements are mechanically deformed to electrically couple the conductors to at least one of the inner elements or the outer elements. In at least some embodiments, the conductors are also electrically coupled to the contact assemblies by physically attaching the conductors to the contact assemblies. In at least some embodiments, the conductors are physically attached to the contact assemblies by one or more heat-related coupling methods.

In at least some embodiments, both inner elements and outer elements are formed from conductive materials. In at least some embodiments, a contact assembly is positioned at an end of a body of an elongated member and one of the conductors is positioned in the contact assembly such that the conductor is either internal or external to the inner element. In at least some embodiments, the outer element is mechanically deformed (e.g., bent, crimped, swaged, folded, creased, or the like) to press against one or more of the conductor and the inner element, thereby electrically coupling the conductor to at least one of the inner element or the outer element. In at least some embodiments, the conductor is also physically attached to one or more of the inner element or the outer element by a heat-related method of coupling (e.g., laser welding, resistance welding, brazing, soldering, or the like), either before or after the outer element is mechanically deformed. In at least some embodiments, the outer element and the inner element are physically attached together (e.g., by a heat-related coupling method) after the outer element is mechanically deformed.

As discussed above, conductors may be disposed along the body of the elongated member in any number of different arrangements including, for example, configured into one or more units, wrapped around a sleeve or mandrel, extending substantially straight, disposed in one or more conductor-carrying elements, or the like. It will be understood that, when one or more conductors are coiled (e.g., configured into one or more units, or the like), the coils may extend to the electrodes, terminals, or both.

Figure 7A:
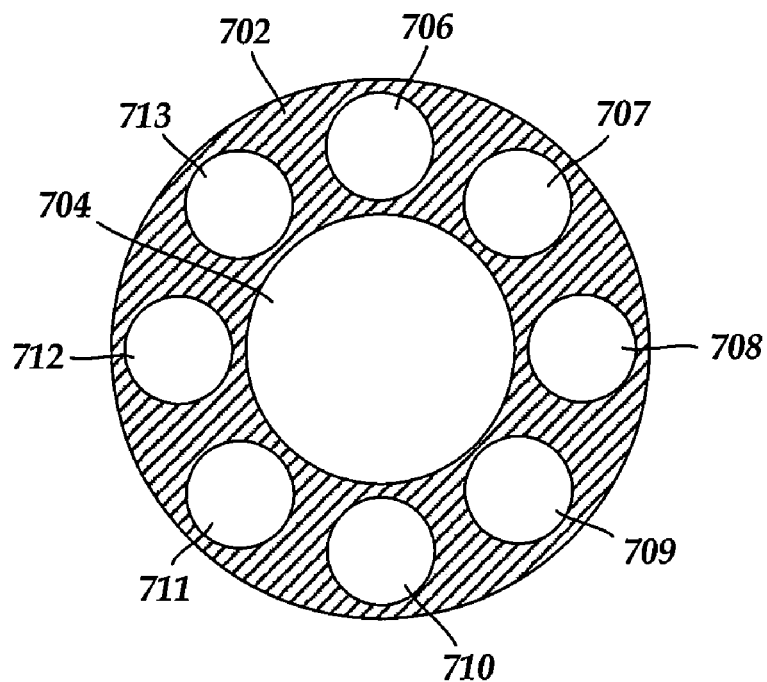
FIG. 7A is a schematic end view of one embodiment of a conductor-carrying element of an electrical stimulation system, according to the invention.

In at least some embodiments, a conductor-carrying element may be used to retain one or more conductors along at least a portion of an elongated member. FIG. 7A is a schematic end view of one embodiment of a conductor-carrying element 702 that includes multiple lumens. The conductor-carrying element 702 defines a central lumen 704 and conductor lumens 706-713. The conductor-carrying element 702 may include many different configurations and many different numbers and sizes of conductor lumens.

Figure 7B:
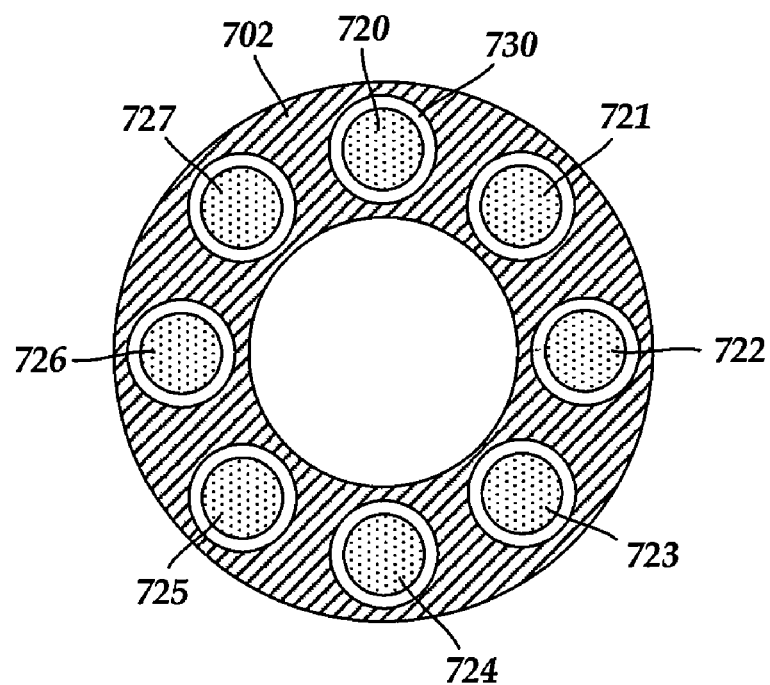
FIG. 7B is a schematic end view of one embodiment of conductors disposed in the conductor-carrying element of FIG. 7A, according to the invention.

In at least some embodiments, one or more conductors extend along at least a portion of a longitudinal length of the lead body within one of the conductor lumens 706-713. In at least some embodiments, ends of the conductors extend from an end of the conductor-carrying element 702. FIG. 7B is a schematic end view of one embodiment of the conductors 720-727 disposed in the conductor-carrying element 702. In at least some embodiments, insulation 730 is disposed around a longitudinal length of one or more of the conductors 720-727. Ends of the conductors 720-727 extend from the end of the conductor-carrying element 702. The extending ends of the conductors 720-727 on one end of the conductor-carrying element 702 are typically coupled to terminals and the extending ends of the conductors 720-727 on the other end of the conductor-carrying element 702 are typically coupled to electrodes (or connector contacts).

A contact assembly may be disposed at one end of the conductor-carrying element 702 which, in turn, may be disposed in a lead body or a lead extension body. The end of one of the conductors 720-727 extending from the conductor-carrying element 702 may be coupled to the conductor assembly. FIGS. 7B-9B show conductors extending along lumens defined in conductor-carrying elements.

In some embodiments, the conductor-carrying element 702 extends the entire length of a lead body (or a lead extension body). In other embodiments, one or more conductor-carrying elements extend along portions of the length of a lead body (or a lead extension body). In at least some embodiments, a lead body (or a lead extension body) also includes one or more outer layers disposed over the one or more conductor-carrying elements. In at least some embodiments, contact assemblies are coupled with conductors that extend along lead bodies (or lead extension bodies) that do not include conductor-carrying elements.

Figure 8A:
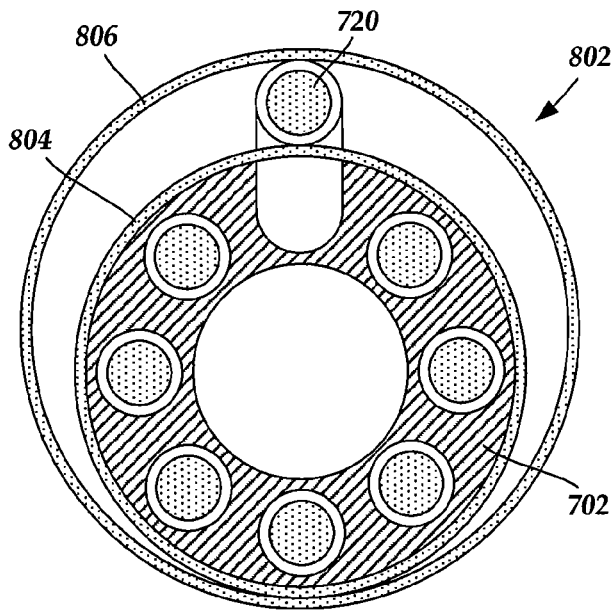
FIG. 8A is a schematic end view of one embodiment of a multi-element contact assembly disposed at one end of the conductor-carrying element of FIG. 7A, one of the conductors of the conductor-carrying element positioned for coupling electrically with the multi-element contact assembly, according to the invention.
Figure 8B:
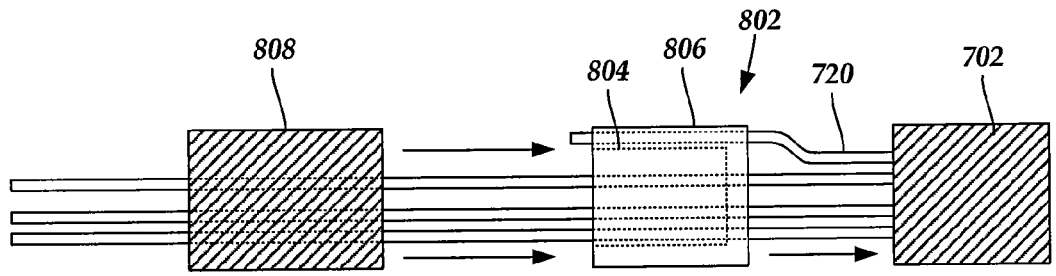
FIG. 8B is a schematic side view of one embodiment of the multi-element contact assembly of FIG. 8A disposed at one end of the conductor-carrying element of FIG. 7A, according to the invention.

FIGS. 8A and 8B are schematic end and side views, respectively, of one embodiment of a first contact assembly 802 disposed at one end of the conductor-carrying element 702. The first contact assembly 802 includes an inner element 804 and an outer element 806. In at least some embodiments, the outer element 806 functions as a contact (e.g., a terminal, an electrode, or the like).

In preferred embodiments, the lead is isodiametric. Accordingly, in at least some embodiments, the outer element 806 has a diameter that is equal to a diameter of a lead body (or a lead extension body). In at least some embodiments, the inner element 804 has a diameter that is equal to the diameter of the conductor-carrying element 702.

The inner element 804 and the outer element 806 can be formed using any rigid or semi-rigid, conductive, biocompatible material. Examples of suitable materials include platinum, iridium, platinum iridium, titanium, alloys of any of the above-listed metals, super alloys (e.g., MP35N and the like), stainless steel, and the like, as well as combinations thereof. It will be understood that the inner element 804 and the outer element 806 may be formed from either the same material or different materials.

In at least some embodiments, the inner element 804 is disposed within the outer element 806 such that the inner element 804 and the outer element 806 are concentric to one another. In at least some embodiments, the outer element 806 is cylindrical. In at least some embodiments, the inner element 804 is also cylindrical. In at least some embodiments, the inner element 804 is C-shaped. In at least some embodiments, the outer element 806 is C-shaped.

In at least some embodiments, the first contact assembly 802 is disposed at one end of the conductor-carrying element 702. In at least some embodiments, one of the conductors 720-727 extending from the end of the conductor-carrying element 702 is coupled to the first contact assembly 802 and the remaining conductors 720-727 are extended through the inner element 804. In at least some embodiments, the remaining conductor 720-727 that extend through the first contact assembly 802 are coupled to one or more additional contacts subsequently positioned laterally from the first contact assembly 802. In FIG. 8B and in other figures, only a few conductors are shown to represent the conductors 721-727, for clarity of illustration.

In FIGS. 8A and 8B, conductor 720 is shown coupled to the first contact assembly 802. The conductor 720 is positioned against the inner element 804 such that the conductor 720 is disposed external to the inner element 804 and internal to the outer element 806. Once the conductor 720 is disposed external to the inner element 804 and internal to the outer element 806, the outer element 806 is deformed (e.g., mechanically deformed) to press the conductor 720 against at least one of the inner element 804 or the outer element 806, thereby electrically coupling the conductor 720 to at least one of the inner element 804 or the outer element 806. In at least some embodiments, the outer element 806 is mechanically deformed (e.g., bent, crimped, swaged, folded, creased, or the like). In at least some embodiment, the conductor 720 is positioned against the inner element 804 such that the conductor 720 is disposed internal to the inner element 804.

In at least some embodiments, the conductor 720 is also electrically coupled to one or more of the inner element 804 or the outer element 806 by physically attaching the conductor 720 to one or more of the inner element 804 or the outer element 806. In at least some embodiments, the conductor 720 is physically attached to one or more of the inner element 804 or the outer element 806 by a heat-related method of attachment (e.g., laser welding, resistance welding, brazing, soldering, or the like). The conductor 720 may be electrically coupled, via the heat-related method of coupling, to one or more of the inner element 804 or the outer element 806 either before or after the conductor 720 is electrically coupled to one or more of the inner element 804 or the outer element 806 by mechanical deformation of the outer element 806. In at least some embodiments, the inner element 804 and the outer element 806 are coupled together, via the heat-related method of coupling, after the conductor 720 is electrically coupled to one or more of the inner element 804 or the outer element 806 by mechanical deformation of the outer element 806.

As discussed above, insulation 730 may be disposed over the longitudinal length of one or more of the conductors 720-727. In at least some embodiments, the insulation 730 of the conductor 720 is removed over at least a portion of the region of the conductor 720 coupled to the first contact assembly 802 prior to mechanical deformation of the outer element 806. In other embodiments, the mechanical deformation process removes enough of the insulation 730 to provide adequate electrical connection between the conductor 720 and at least one of the inner element 804 or the outer element 806 without needing to remove a portion of the insulation 730 prior to performing the mechanical deformation process.

In at least some embodiments, once a first end of the first contact assembly 802 is positioned against the conductor-carrying element 702 and an electrical connection is made between the conductor 720 and the first contact assembly 802, a spacer 808 may be positioned adjacent to a second end of the first contact assembly 802 opposite to the first end. The conductors 721-727 extending through the inner element 804 of the contact assembly 802 also extend through the spacer 808. In at least some embodiments, when a tip (not shown) of the conductor 720 extends beyond the second end of the first contact assembly 802, the tip of the conductor 720 may be removed or bent so that the tip of the conductor 720 does not obstruct the spacer 808 from abutting the first contact assembly 802.

An additional contact assembly may be positioned at the opposite end of the spacer from the first contact assembly and another conductor may be coupled to the additional contact assembly. It will be understood that any number of contact assemblies may be coupled to conductors and separated from one another by spacers. In at least some embodiments, the number of contact assemblies is equal to the number of conductors. It will further be understood that the same process may be repeated on an opposing end of the conductor-carrying element 702.

Figure 8C:
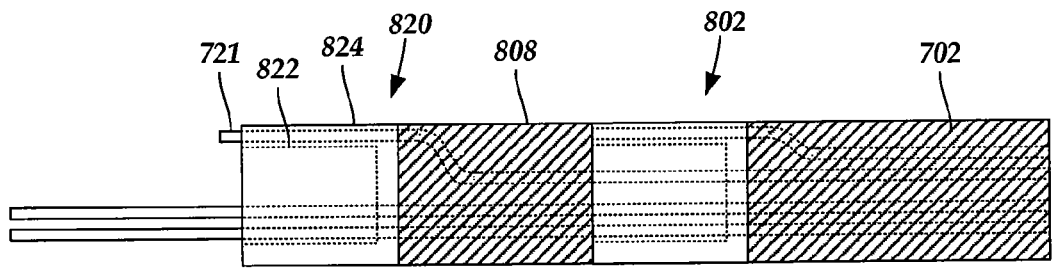
FIG. 8C is a schematic side view of one embodiment of a second multi-element contact assembly disposed at one end of the conductor-carrying element of FIG. 7A, according to the invention.

FIG. 8C is a schematic side view of one embodiment of a second contact assembly 820 disposed at one end of the conductor-carrying element 702. The conductor 721 is positioned between, and electrically coupled to, an inner element 822 and an outer element 824 of the second contact assembly 820. The remaining conductors 722-727 extend through the inner element 822. The spacer 808 separates the first contact assembly 802 from the second contact assembly 820.

In at least some embodiments, the outer elements 806 and 824 both function as terminals or both function as electrodes. In preferred embodiments, if one or more additional contact assemblies are disposed on the same end of the conductor-carrying element 702 and separated from one another by spacers, the outer element(s) of those additional contact assemblies also function as outer elements 806 and 824. In at least some embodiments, one or more contact assemblies disposed on the opposite end of the conductor-carrying element 702 each have outer elements that function as the other of either terminals or electrodes, depending on the functionality of the outer elements 806 and 824.

In an alternate embodiment, a conductor is physically attached to a C-shaped inner element via a heat-related method of coupling. An outer element is then disposed over the inner element (and the electrically coupled conductor), and at least a portion of the outer element and the inner element are physically attached together. In at least some embodiments, the inner element is substantially flat when the conductor is physically attached to the inner element. In which case, the inner element is bent into a "C" shape after the physical attachment of the conductor to the inner element. In some embodiments, the conductor is electrically coupled to an inner surface of the inner element. In other embodiments, the conductor is electrically coupled to an outer surface of the inner element.

Figure 9A:
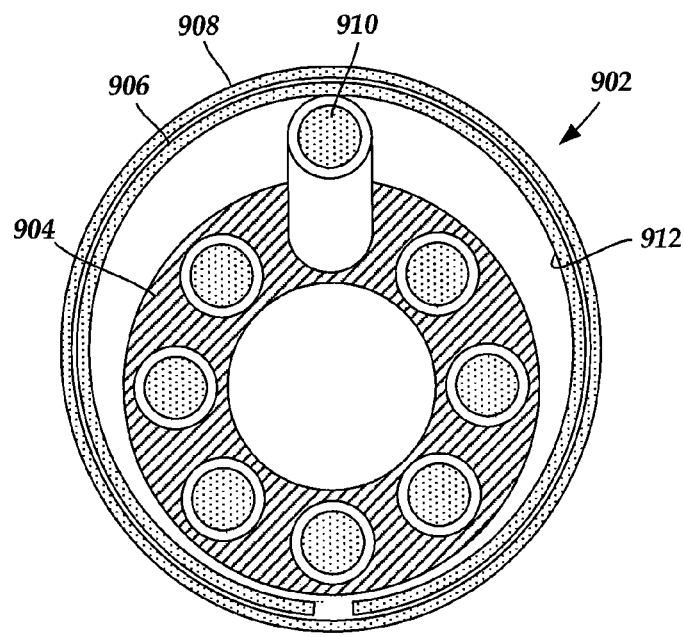
FIG. 9A is a schematic end view of one embodiment of a multi-element contact assembly disposed at one end of a conductor-carrying element, one of the conductors of the conductor-carrying element positioned for coupling electrically with the multi-element contact assembly, according to the invention.
Figure 9B:
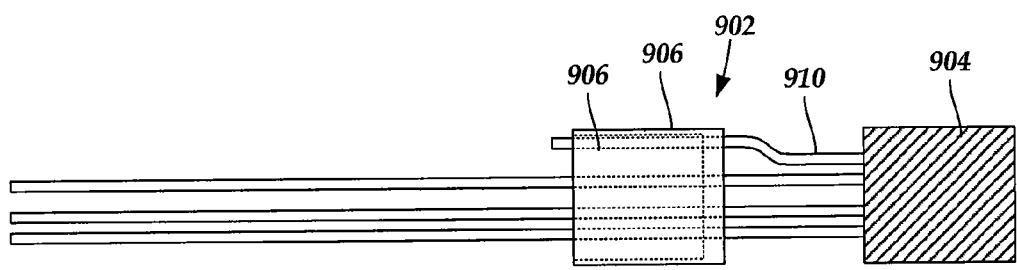
FIG. 9B is a schematic side view of one embodiment of the multi-element contact assembly of FIG. 9A disposed at one end of the conductor-carrying element of FIG. 9A, according to the invention.

FIG. 9A is a schematic end view of one embodiment of a contact assembly 902 disposed at one end of a conductor-carrying element 904. The contact assembly 902 includes a C-shaped inner element 906 and a cylindrical outer element 908. Conductors, such as conductor 910, are disposed in the conductor-carrying element 904. FIG. 9B is a schematic side view of one embodiment of the contact assembly 902 disposed at one end of the conductor-carrying element 904 and the conductor 910 coupled to the inner element 906 which, in turn, is coupled to the outer element 908. In preferred embodiments, the diameter of the outer element 908 is equal to the diameter of a lead body (or lead extension body) in which the conductor-carrying element 904 is disposed.

In FIGS. 9A and 9B, the conductor 910 is shown electrically coupled to an inner surface 912 of the inner element 906. It will be understood that the conductor 910 may, instead, be electrically coupled to an outer surface of the inner element 906. In at least some embodiments, the outer element 908 is disposed over the inner element 906 such that the inner element 906 is compressed within the outer element 908.

Once the outer element 908 is disposed over the inner element 906, the outer element 908 is electrically coupled to the inner element 906. In some embodiments, the outer element 908 is mechanically deformed to press against the inner element 906. In other embodiments, the outer element is physically attached to the inner element 906 by a heat-related method of coupling (e.g., laser welding, resistance welding, brazing, soldering, or the like). In at least some embodiments, the outer element 908 and the inner element 906 are electrically coupled by both mechanical deformation of the outer element 908 and physical attachment.

In at least some embodiments, each of the conductors of the conductor-carrying element 904 are physically attached to a different inner element. The inner elements are arranged along an axis of the end of the conductor-carrying element 904 such that the conductors coupled to the more lateral inner elements extend through each of the more medial inner elements. Outer elements are positioned over, and electrically coupled to, each inner element. In at least some embodiments, at least one of the elements may be closed to form a continuous transverse path.

In at least some embodiments, the inner element 906 has a longitudinal length 914 (shown in FIG. 9B as a two-headed arrow) that is not equal to a longitudinal length 916 (also shown in FIG. 9B as a two-headed arrow) of the outer element 908. In at least some embodiments, the longitudinal length 916 of the outer element 908 is greater than the longitudinal length 914 of the inner element 906. It may be an advantage to have the outer element 908 of the contact assembly 902 being greater in length than the inner element 906 so that, when the conductor 910 is coupled to the inner element 906, but not yet coupled to the outer element 908, the axial positioning of the inner element 906 may be adjusted without needing to axially adjust the outer element 908. Thus, the outer element 908 may be positioned as desired without needing to axially adjust the outer element 908 to accommodate the positioning of the electrical coupling of the outer element 908 with the conductor 910.

Figure 10:
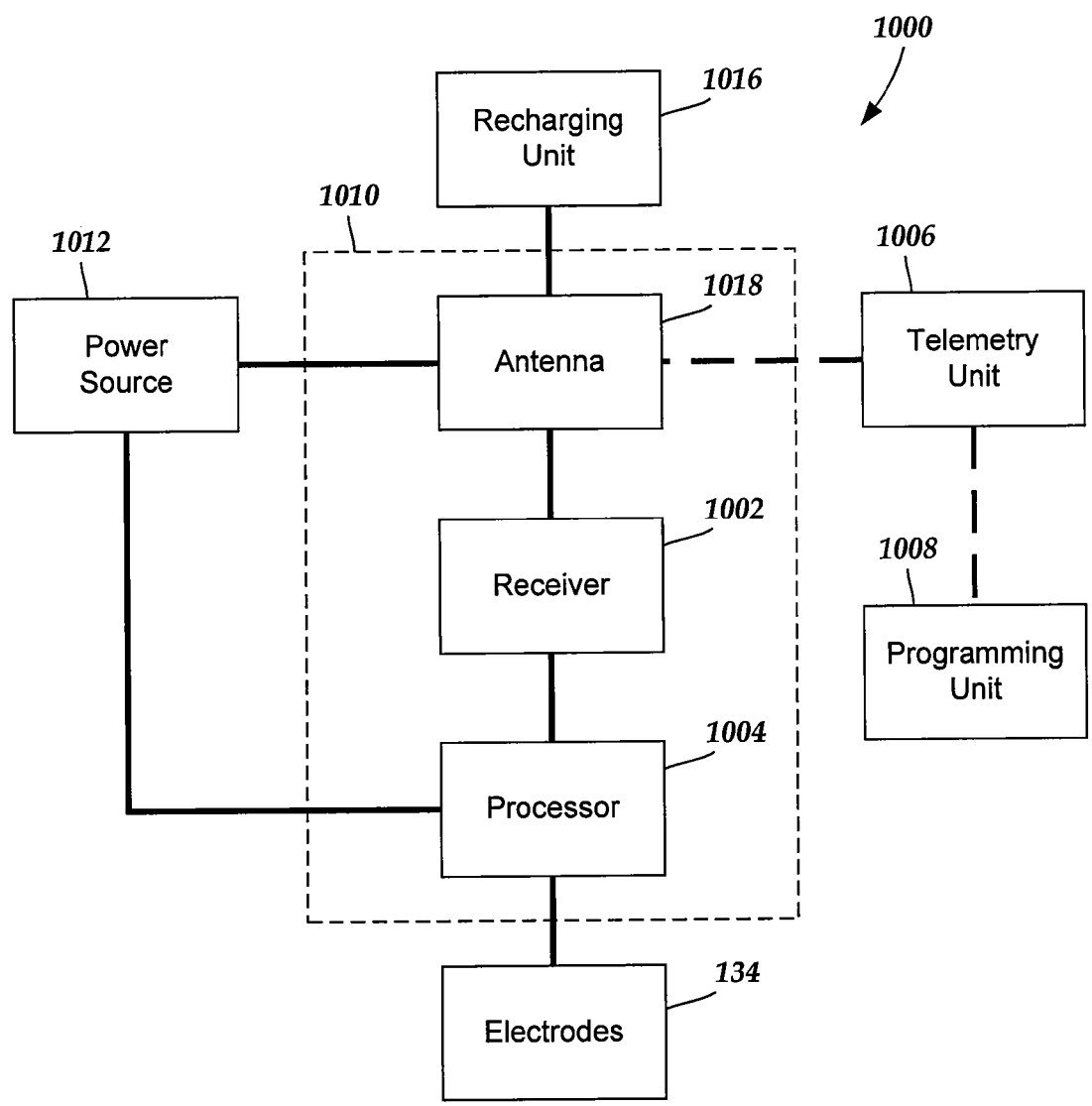
FIG. 10 is a schematic overview of one embodiment of components of a stimulation system, including an electronic subassembly disposed within a control module, according to the invention.

FIG. 10 is a schematic overview of one embodiment of components of an electrical stimulation system 1000 including an electronic subassembly 1010 disposed within a control module. It will be understood that the electrical stimulation system can include more, fewer, or different components and can have a variety of different configurations including those configurations disclosed in the stimulator references cited herein.

Some of the components (for example, power source 1012, antenna 1018, receiver 1002, and processor 1004) of the electrical stimulation system can be positioned on one or more circuit boards or similar carriers within a sealed housing of an implantable pulse generator, if desired. Any power source 1012 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1018 or a secondary antenna. The external power source can be in a device that is mounted on the skin of the user or in a unit that is provided near the user on a permanent or periodic basis.

If the power source 1012 is a rechargeable battery, the battery may be recharged using the optional antenna 1018, if desired. Power can be provided to the battery for recharging by inductively coupling the battery through the antenna to a recharging unit 1016 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1004 is generally included to control the timing and electrical characteristics of the electrical stimulation system. For example, the processor 1004 can, if desired, control one or more of the timing, frequency, strength, duration, and waveform of the pulses. In addition, the processor 1004 can select which electrodes can be used to provide stimulation, if desired. In some embodiments, the processor 1004 may select which electrode(s) are cathodes and which electrode(s) are anodes. In some embodiments, the processor 1004 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1008 that, for example, allows modification of pulse characteristics. In the illustrated embodiment, the processor 1004 is coupled to a receiver 1002 which, in turn, is coupled to the optional antenna 1018. This allows the processor 1004 to receive instructions from an external source to, for example, direct the pulse characteristics and the selection of electrodes, if desired.

In one embodiment, the antenna 1018 is capable of receiving signals (e.g., RF signals) from an external telemetry unit 1006 which is programmed by a programming unit 1008. The programming unit 1008 can be external to, or part of, the telemetry unit 1006. The telemetry unit 1006 can be a device that is worn on the skin of the user or can be carried by the user and can have a form similar to a pager, cellular phone, or remote control, if desired. As another alternative, the telemetry unit 1006 may not be worn or carried by the user but may only be available at a home station or at a clinician's office. The programming unit 1008 can be any unit that can provide information to the telemetry unit 1006 for transmission to the electrical stimulation system 1000. The programming unit 1008 can be part of the telemetry unit 1006 or can provide signals or information to the telemetry unit 1006 via a wireless or wired connection. One example of a suitable programming unit is a computer operated by the user or clinician to send signals to the telemetry unit 1006.

The signals sent to the processor 1004 via the antenna 1018 and receiver 1002 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1000 to cease operation, to start operation, to start charging the battery, or to stop charging the battery. In other embodiments, the stimulation system does not include an antenna 1018 or receiver 1002 and the processor 1004 operates as programmed.

Optionally, the electrical stimulation system 1000 may include a transmitter (not shown) coupled to the processor 1004 and the antenna 1018 for transmitting signals back to the telemetry unit 1006 or another unit capable of receiving the signals. For example, the electrical stimulation system 1000 may transmit signals indicating whether the electrical stimulation system 1000 is operating properly or not or indicating when the battery needs to be charged or the level of charge remaining in the battery. The processor 1004 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable lead comprising:
an isodiametric lead body having a distal end, a proximal end, and a longitudinal length;
a plurality of electrodes disposed on the distal end of the lead body;
a plurality of terminals disposed on the proximal end of the lead body;
a plurality of conductors disposed in the lead body, each conductor electrically coupling at least one of the electrodes to at least one of the terminals;
the lead body comprising
a single-piece conductor-carrying element extending along at least a portion of the longitudinal length of the lead body, the conductor-carrying element having a diameter, a first end, and an opposing second end, the conductor-carrying element defining a plurality of conductor lumens extending from the first end to the second end, wherein the plurality of conductors extend along the plurality of conductor lumens from the first end of the conductor-carrying element to the second end of the conductor-carrying element with one end of each of the plurality of conductors extending outwardly from the first end, and at least one outer layer disposed over the conductor-carrying element, the at least one outer layer having an outer diameter;

wherein at least one of the electrodes or at least one of the terminals comprises a multi-element contact assembly disposed at the first end of the conductor-carrying element, the multi-element contact assembly comprising at least one conductive inner element having a diameter, an interior surface, and an exterior surface, and at least one conductive outer element having a diameter, the at least one outer element disposed over the inner element;

wherein for one of the plurality of conductors the end of the conductor extending outwardly from the first end of the conductor-carrying element is electrically coupled to one of the multi-element contact assemblies with the extended end of the conductor positioned against the exterior surface of the at least one inner element, and wherein the at least one outer element comprises a region that is in contact with the at least one inner element;

wherein the diameter of the conductor-carrying element is equal to the diameter of the inner element;

wherein the outer diameter of the at least one outer layer of the lead body is equal to the diameter of the outer element.

2. The lead of claim 1, wherein the at least one of the plurality of conductors is also electrically coupled to the one of the multi-element contact assemblies by physically attaching the at least one of the plurality of conductors to at least one of the at least one inner element or the at least one outer element.

3. The lead of claim 2, wherein the at least one of the plurality of conductors is physically attached to at least one of the at least one inner element or the at least one outer element by at least one of laser welding, resistance welding, brazing, or soldering the at least one of the plurality of conductors to at least one of the at least one inner element or the at least one outer element.

4. The lead of claim 1, wherein the region of the at least one outer element in contact with the at least one inner element is mechanically deformed to electrically couple the at least one of the plurality of conductors to at least one of the at least one inner element or the at least one outer element.

5. The lead of claim 1, wherein the at least one inner element is physically attached to the at least one outer element.

6. The implantable lead of claim 1, wherein the multi-element contact assembly physically abuts the first end of the conductor-carrying element.

7. The lead of claim 1, wherein the at least one inner element is cylindrical.

8. The lead of claim 1, wherein the at least one inner element is C-shaped.

9. The lead of claim 1, wherein the at least one inner element has a longitudinal length that is different from a longitudinal length of the at least one outer element.

10. An electrical stimulating system comprising:
the lead of claim 1;
a control module configured and arranged to electrically couple to the proximal end of the lead, the control module comprising
a housing, and
an electronic subassembly disposed in the housing; and
a connector configured and arranged for receiving the lead, the connector having a proximal end, a distal end, and a longitudinal length, the connector comprising
a connector housing defining a port at the distal end of the connector, the port configured and arranged for receiving the proximal end of the lead body, and
a plurality of connector contacts disposed in the connector housing, the connector contacts configured and arranged to couple to at least one of the plurality of terminals disposed along the proximal end of the lead body.

11. The electrical stimulating system of claim 10, further comprising a lead extension having a proximal end and a distal end, the connector disposed on the distal end of the lead extension.

12. The electrical stimulating system of claim 11, wherein the lead extension comprises;
a lead extension body having a distal end, a proximal end, and a longitudinal length;
a plurality of connector contacts disposed on the distal end of the lead extension body;
a plurality of lead extension terminals disposed on the proximal end of the lead extension body; and
a plurality of lead extension conductors disposed in the lead extension body, each lead extension conductor electrically coupling at least one of the connector contacts to at least one of the lead extension terminals;
wherein at least one of the lead extension terminals comprises a multi-element contact assembly, the multi-element contact assembly comprising
at least one conductive inner element having an interior surface and an exterior surface, and
at least one conductive outer element disposed over the inner element;
wherein at least one of the plurality of lead extension conductors is electrically coupled to one of the multi-element contact assemblies with the at least one of the plurality of lead extension conductors positioned against the exterior surface of the at least one inner element, and wherein the at least one outer element comprises a region that is in contact with the at least one inner element.

13. The electrical stimulating system of claim 10, wherein the connector is disposed on the control module.

14. A method for forming an implantable lead, the method comprising:
providing an isodiametric lead body, the lead body comprising a single-niece conductor-carrying element and at least one outer layer disposed over the conductor-carrying element;
disposing a plurality of elongated conductors into conductor lumens defined along an entire length of the single-piece conductor-carrying element, the conductor-carrying element having opposing first and second ends and a diameter, wherein one end of each of the plurality of conductors extends outwardly from the conductor lumens at the first end of the conductor-carrying element;
disposing a multi-element contact assembly at the first end of the conductor-carrying element, the multi-element contact assembly comprising at least one inner element having a diameter, an interior surface, and an exterior surface and at least one outer element having a diameter, the at least one outer element disposed over the inner element, wherein the diameter of the conductor-carrying element is equal to the diameter of the inner element, and wherein the outer diameter of the at least one outer layer of the lead body is equal to a diameter of the outer element;

for one of the plurality of conductors disposing the end extending outwardly from the first end of the conductor-carrying element into the multi-element contact assembly with the extended end of the conductor positioned against the exterior surface of the at least one inner element; and contacting a region of the at least one outer element with the at least one inner element.

15. The method of claim 14, further comprising for each of the remaining plurality of conductors passing the extended ends of the conductors through a portion of the multi-element contact assembly that is internal to the at least one inner element.

16. The method of claim 15, further comprising for each of the remaining plurality of conductors passing the extended ends of the conductors through a spacer positioned at an end of the multi-element contact assembly opposite to the lead body and electrically coupling at least one of the remaining conductors to another multi-element contact assembly disposed at an opposite end of the spacer.

17. The method of claim 14, further comprising physically attaching the at least one inner element to the at least one outer element by at least one of laser welding, resistance welding, brazing, or soldering the conductor to the outer element.

18. A method for forming an implantable lead, the method comprising:

providing an isodiametric lead body, the lead body comprising a single-piece conductor-carrying element and at least one outer layer disposed over the conductor-carrying element;

disposing a plurality of elongated conductors into conductor lumens defined along an entire length of a single-piece conductor-carrying element, the conductor-carrying element having opposing first and second ends, wherein one end of each of the plurality of conductors extends outwardly from the conductor lumens at the first end of the conductor-carrying element;

physically attaching each of the ends of the conductors extending from the first end of the conductor carrying element to a different one of a plurality of longitudinally-spaced-apart inner elements disposed at the first end of the conductor-carrying element, wherein for each of the conductors the extended end of the conductor is physically attached to the different one of the plurality of inner elements with the entire conductor being disposed external to that inner element, wherein a diameter of the conductor-carrying element is equal to a diameter of at least one of the plurality of inner elements;

disposing individually a different one of a plurality of outer elements over each of the inner elements to form a plurality of multi-element contact assemblies, each of the multi-element contact assemblies comprising a one of the outer elements disposed around a one of the inner elements, wherein the outer diameter of the at least one outer layer of the lead body is equal to a diameter of at least one of the plurality of outer elements; and contacting each of the inner elements of the multi-element contact assemblies to the corresponding outer elements.

19. The method of claim 18, wherein physically attaching each of the ends of the conductors extending from the first end of the conductor-carrying element to a different one of the plurality of inner elements comprises at least one of the plurality of inner elements being substantially planar when the conductor is physically attached to the at least one inner element and the at least one inner element being subsequently bent into a C-shape.

20. The method of claim 18, wherein physically attaching each of the ends of the conductors extending from the first end of the conductor-carrying element to a different one of the plurality of inner elements comprises at least one of laser welding, resistance welding, brazing, or soldering the inner element to the corresponding outer element.

21. The method of claim 18, wherein contacting each of the inner elements of the multi-element contact assemblies to the corresponding outer elements comprises mechanically deforming the outer element such that the conductor contacts at least one of the inner surface or the outer surface of the inner element.

* * * * *